United States Patent
Abruzzo

(10) Patent No.: US 12,220,540 B2
(45) Date of Patent: Feb. 11, 2025

(54) ANTI-REFLUX PLUG FORMING DETACHABLE TIP MICROCATHETER

(71) Applicant: Phoenix Children's Hospital, Inc., Phoenix, AZ (US)

(72) Inventor: Todd Abruzzo, Paradise Valley, AZ (US)

(73) Assignee: Phoenix Children's Hospital, Inc., Phoenix, AZ (US)

( * ) Notice: Subject to any disclaimer, the term of this patent is extended or adjusted under 35 U.S.C. 154(b) by 229 days.

(21) Appl. No.: 17/542,166

(22) Filed: Dec. 3, 2021

(65) Prior Publication Data
US 2022/0175385 A1    Jun. 9, 2022

Related U.S. Application Data

(60) Provisional application No. 63/165,655, filed on Mar. 24, 2021, provisional application No. 63/121,586, filed on Dec. 4, 2020.

(51) Int. Cl.
*A61M 25/00* (2006.01)
*A61B 17/12* (2006.01)
*A61M 25/01* (2006.01)

(52) U.S. Cl.
CPC ... *A61M 25/0074* (2013.01); *A61B 17/12031* (2013.01); *A61B 17/12109* (2013.01);
(Continued)

(58) Field of Classification Search
CPC ........ A61B 17/12031; A61B 17/12109; A61B 17/12181; A61B 17/12186;
(Continued)

(56) References Cited

U.S. PATENT DOCUMENTS 3,736,939 A * 6/1973 Taylor .................. A61M 25/10
604/275
4,936,835 A * 6/1990 Haaga ................ A61B 10/0233
604/265

(Continued)

FOREIGN PATENT DOCUMENTS

WO    WO-2018187577 A2 * 10/2018 ............ A61M 25/00

*Primary Examiner* — Kami A Bosworth
(74) *Attorney, Agent, or Firm* — Messner Reeves LLP

(57) ABSTRACT

A medical device and methods of use are disclosed herein. The medical device includes a base microcatheter and a microcatheter tip assembly detachably coupled to a first end of the base microcatheter. The microcatheter tip assembly includes a body defining at least one lateral hole and a loading region, and an opening in a first end of the microcatheter tip assembly. The medical device includes a membrane carrier disposed within the loading region of the microcatheter tip assembly. The membrane carrier includes a body defining an opening, and a membrane covering the opening in the membrane carrier. The membrane is configured to rupture in response to a force applied to the membrane. When the membrane is disposed within the loading region of the microcatheter tip assembly and the membrane is not ruptured, the membrane is configured to prevent the flow of material through the opening in the first end of the microcatheter tip assembly.

18 Claims, 18 Drawing Sheets

(52) U.S. Cl.
CPC ... *A61B 17/12186* (2013.01); *A61M 25/0021* (2013.01); *A61M 25/0108* (2013.01); *A61B 2017/1205* (2013.01); *A61M 2025/0042* (2013.01); *A61M 25/007* (2013.01)

(58) Field of Classification Search
CPC ...... A61B 17/12195; A61B 2017/1205; A61B 18/1492; A61M 25/0069; A61M 25/007; A61M 25/0074; A61M 25/0075; A61M 2025/0018; A61M 2025/0042; A61M 2025/0073; A61M 2025/0079; A61M 39/221; A61M 2039/222
See application file for complete search history.

(56) References Cited

U.S. PATENT DOCUMENTS

| | | | | |
|---|---|---|---|---|
| 5,066,278 | A * | 11/1991 | Hirschberg | A61M 25/0045 604/890.1 |
| 7,481,798 | B2 * | 1/2009 | Rioux | A61M 25/0084 604/264 |
| 9,468,739 | B2 * | 10/2016 | Sutherland | A61B 17/12109 |
| 2016/0106584 | A1 * | 4/2016 | Andino | A61M 5/19 604/87 |
| 2017/0368306 | A1 * | 12/2017 | Tal | A61M 25/0074 |
| 2018/0049860 | A1 * | 2/2018 | Tal | A61B 17/12181 |

* cited by examiner

ANTI-REFLUX PLUG FORMING DETACHABLE TIP MICROCATHETER

CROSS-REFERENCES TO RELATED APPLICATIONS

This patent application claims priority to U.S. Provisional Patent Application No. 63/121,586 filed on Dec. 4, 2020 and entitled "Anti-Reflux Plug Forming Detachable Tip Microcatheter" and U.S. Provisional Patent Application No. 63/165,655 filed on Mar. 24, 2021 and entitled "Anti-Reflux Plug Forming Detachable Tip Microcatheter", the entire contents of which are hereby incorporated by reference.

STATEMENT REGARDING FEDERALLY SPONSORED RESEARCH

Not Applicable.

FIELD OF THE INVENTION

Staggered dual exit port microcatheter with distal tip membrane and shaft mounted flow disruptor to promote efficient and reliable formation of anti-reflux plug during embolization in a manner that allows "pressure cooker" style embolization with liquid embolic agents using a solitary single lumen microcatheter.

BACKGROUND OF THE INVENTION

Embolization of arteriovenous malformations (AVMs) may involve deposition of a liquid embolic agent into or proximate to the malformations via microcatheter. Conventional microcatheter designs deposit embolic agent via the microcatheter's distal lumen end hole. In some cases, the embolic agent, once deposited, instead of flowing directly towards the malformation, may flow backwards away from the distal end of the microcatheter and the malformation. This reflux flow can cause complications. In order to prevent excess reflux, it is necessary to pause injection of liquid embolic agent and allow refluxing material to solidify. An unintended consequence of pausing the injection is solidification of the front edge of liquid embolic agent advancing into the malformation. This results in an anterograde flow lock that prevents further entry of liquid embolic agent into the malformation.

SUMMARY OF THE INVENTION

The present invention provides, in an embodiment, a medical device including a base microcatheter, and a microcatheter tip assembly detachably coupled to a first end of the base microcatheter. The microcatheter tip assembly includes a body defining at least one lateral hole and a loading region, and an opening in a first end of the microcatheter tip assembly. The medical device includes a membrane carrier disposed within the loading region of the microcatheter tip assembly. The membrane carrier includes a body defining an opening, and a membrane covering the opening in the membrane carrier. The membrane is configured to rupture in response to a force applied to the membrane, wherein, when the membrane is disposed within the loading region of the microcatheter tip assembly and the membrane is not ruptured, the membrane is configured to prevent the flow of material through the opening in the first end of the microcatheter tip assembly.

The present invention provides, in another embodiment, a medical device including a catheter tip assembly configured to couple to an end of a catheter. The catheter tip assembly includes a body defining at least one lateral hole and a loading region, and an opening in a first end of the catheter tip assembly. The medical device includes a membrane carrier configured to be within the loading region of the catheter tip assembly. The membrane carrier includes a body defining an opening, and a membrane covering the opening in the membrane carrier. The membrane is configured to rupture in response to a force applied to the membrane.

The present invention provides, in another embodiment, a method including inserting a medical device into a vessel. The medical device includes a base catheter and a detachable tip assembly that is removably coupled to the base catheter. The detachable tip assembly includes a plurality of lateral holes. The method includes flowing an embolic material through the base catheter, the detachable tip assembly, and the plurality of lateral holes to form an anti-reflux plug in the vessel around at least a portion of the detachable tip assembly, flowing the embolic material through an end hole of the detachable tip assembly anterograde to the anti-reflux plug, detaching the detachable tip assembly from the base catheter, and removing the base catheter from the vessel.

These and other features, aspects, and advantages of the present invention will become better understood upon consideration of the following detailed description, drawings and appended claims.

BRIEF DESCRIPTION OF THE DRAWINGS

FIG. 3 depicts the parachute structure in a closed configuration, while FIG. 4 depicts the parachute structure in an open or deployed configuration.

DETAILED DESCRIPTION OF THE INVENTION

Figure 1:
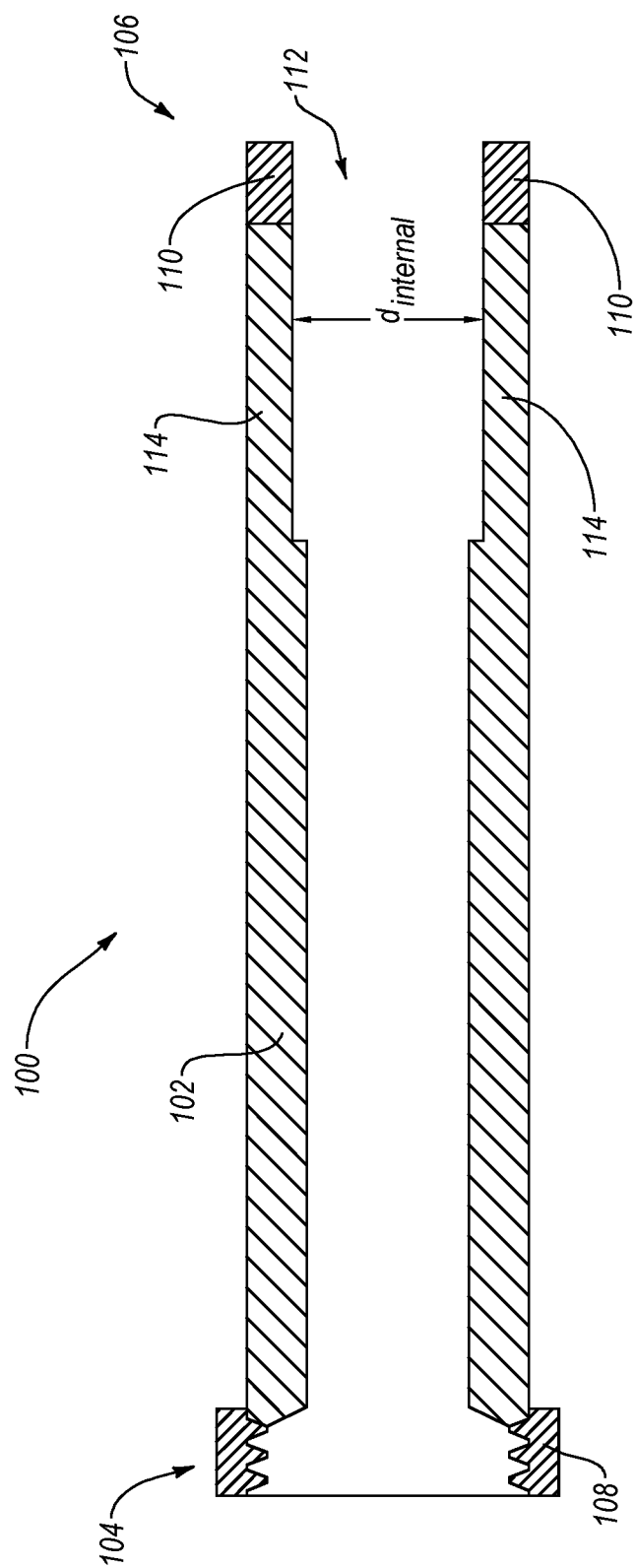
FIG. 1 is a cross-sectional view of a base microcatheter of the present disclosure, wherein the base microcatheter includes an internally beveled surface configured to engage a detachable tip.

The present invention will now be discussed in detail with regard to the attached drawing figures that were briefly described above. In the following description, numerous specific details are set forth illustrating the Applicant's best mode for practicing the invention and enabling one of ordinary skill in the art to make and use the invention. It will be obvious, however, to one skilled in the art that the present invention may be practiced without many of these specific details. In other instances, well-known machines, structures, and method steps have not been described in particular detail in order to avoid unnecessarily obscuring the present invention. Unless otherwise indicated, like parts and method steps are referred to with like reference numerals.

Various medical conditions may be treated by the deposition of a liquid embolic agent via microcatheter. Microcatheters are catheters that can be used to access distal anatomy, deliver therapeutic embolic agents, inject contrast media and perform other procedures within complex endovascular anatomy. In general, microcatheters can be catheters with relatively small outer diameters (e.g., less than 1 millimeters (mm) or 3 French) as compared to conventional catheters. For example, arteriovenous malformations (AVM) of the brain are the most common cause of hemorrhagic stroke in the first two decades of life. Hemorrhagic stroke is a life threatening condition characterized by bleeding into and around the brain.

The clinical management of patients with brain AVM typically involves a multimodal approach designed to exclude the AVM from the circulatory system so that blood is no longer able to circulate into the malformation. When blood is not able to circulate into an AVM, the AVM cannot bleed.

A brain AVM can be isolated from the circulatory system by surgically removing it, by exposing it to a very high dose of focused radiation (stereotactic radiosurgery) or by performing an embolization procedure.

In modern neurosurgical practice, brain AVM embolization is performed by injecting liquid copolymer agents into the lumen of AVM blood vessels through indwelling transarterial microcatheters. The procedure is performed with the guidance of fluoroscopy, a type of high speed, high resolution x-ray based medical imaging technology.

The embolization process is initiated by introducing a microcatheter into one of the major brain arteries. The microcatheter is then navigated into an AVM blood vessel using fluoroscopic guidance. Liquid embolic agent (e.g., a liquid embolic agent comprising ethylene vinyl alcohol (EVOH)) is delivered into the AVM blood vessel by injecting the liquid embolic agent through the microcatheter tip end hole and into the AVM blood vessel. Various embolic agents may be utilized in conjunction with the present microcatheter system, including cohesive (EvOH) and/or adhesive-type (acrylics) agents.

As the embolic agent exits the microcatheter tip end hole and enters the bloodstream the embolic agent begins to solidify. The embolic agent material characteristically moves through the blood vessel as the material solidifies. When the leading end of the advancing column of material becomes sufficiently thick, the resistance to anterograde movement exceeds the resistance of retrograde movement. This can result in reflux of copolymer around the tip of the microcatheter. The process of copolymer embolic material "solidification" is progressive, centripetal, and longitudinally asymmetric such that the leading distal face of the advancing column of embolic material exiting the microcatheter tip end hole remains in a fluid state for a longer period of time than the proximal end of the column. If the embolic copolymer material injection is continued without interruption, the material will keep moving in retrograde fashion until the material blocks flow in a major upstream brain artery, potentially causing medical complications. Excessively refluxed embolic material may also permanently entrap the microcatheter in the patient.

If the embolic copolymer injection is paused long enough for refluxed material around the microcatheter tip to form a solid plug, this may enable resumption of anterograde movement of copolymer into AVM vessels until the resistance to anterograde flow once again exceeds the resistance to retrograde flow. The solid plug that forms around the microcatheter tip does not initially occupy the full luminal cross-section of the microcatheter bearing vessel. Consequently, many cycles of copolymer injection and pausing may be required to establish a copolymer plug that is highly resistant to reflux. In some cases, the microcatheter tip end hole becomes permanently obstructed by solidified copolymer agent before an adequate anti-reflux plug is created. This can prevent penetration of the liquid copolymer agent into all of the AVM vessels.

Dual lumen balloon occlusion catheters are sometimes used to establish an anti-reflux boundary in an AVM access vessel however occlusion balloons have proven to be an unreliable form of anti-reflux protection. Even balloons that are overinflated in a vessel will allow pressurized liquid copolymer to escape between the surface of the occlusion balloon and the adjacent vessel wall. Furthermore, dual lumen catheters are by necessity larger and stiffer than single lumen microcatheters. Consequently, in contrast to single lumen microcatheters, dual lumen catheters cannot safely be placed into the relatively small, distal and tortuous brain vessels that require catheterization for AVM embolization. A single lumen, flexible, low profile microcatheter system that consistently produces a solid, highly reflux resistant copolymer plug around the distal tip of the microcatheter, before the distal orifice of the microcatheter end hole and AVM access vessel become obstructed by solidified copolymer would enable a much more effective embolization treatment of brain AVM or other conditions.

The present disclosure provides a detachable-tip microcatheter system that can be used to deliver liquid copolymer embolic agent (e.g., into a 1-4 mm vessel) in stepwise fashion. The detachable microcatheter tip of the present microcatheter system includes a shaft-mounted flow disruptor, one or more side-holes for exit of liquid copolymer, and one or more pressure sensitive membranes covering a distal end-hole of the detachable microcatheter tip.

During use of the microcatheter system, embolic agent initially flows out of the one or more side-holes to form an anti-reflux plug. At that time, flow of embolic agent out of the distal end-hole of the detachable microcatheter tip is inhibited by a pressure sensitive membrane or other structure covering the distal end-hole or otherwise obstructing liquid embolic agent flow through the distal end-hole. As liquid embolic agent initially exits the side holes of the detachable tip of the microcatheter system, the embolic agent flow through the side holes exerts pressure on the shaft mounted flow disruptor (initially in the closed configuration), where the shaft mounted flow disruptor is opposed to the shaft of the detachable tip, covering or overlaying the side holes. The pressure exerted by the liquid embolic agent flowing through the side holes triggers or otherwise initiates opening or deployment of the flow disruptor. With the flow disruptor in an opened or at least partially opened configuration, the flow disruptor thereby prevents liquid embolic agent exiting the side holes from being carried downstream into the surrounding blood flow. The liquid embolic agent contained by the deployed and overhanging flow disruptor thereby forms into a coherent anti-reflux plug structure that grows by the addition of new liquid embolic agent material through the detachable tip side holes around the circumference of the microcatheter detachable tip. The anti-reflux plug progressively enlarges until the anti-reflux plug fills the entire cross section of the blood vessel enclosing the detachable microcatheter tip. As the anti-reflux plug grows, the anti-reflux plug asymmetrically hardens in centripetal fashion, from distal to proximal regions.

When the anti-reflux plug has grown to fully occlude the cross-sectional area of the surrounding blood vessel, and has uniformly hardened, further flow of the liquid embolic agent out of the one or more side-holes is inhibited. At this time, flow of embolic agent out of the distal end-hole is desired. In order to establish flow of liquid embolic agent through the end hole of the detachable tip, the injection pressure used to deliver liquid embolic agent into the microcatheter can be increased (e.g., in embodiments into an injection pressure range of 100 to 500 pounds per square inch, though in other embodiments different injection pressure may be utilized) to cause rupture or displacement of the membrane or structure otherwise sealing the end hole of the detachable tip allowing the liquid embolic agent to flow out of the distal end hole of the microcatheter. When the procedure is complete, the detachable microcatheter tip and affixed flow disruptor, in embodiments that possess a flow disruptor, (which may now be adhered-to by the embolic agent), can be separated from the main shaft of the microcatheter thereby enabling the base microcatheter to be withdrawn from the procedure site. The detachable microcatheter tip and affixed flow disruptor remain implanted in situ.

FIG. 1 is a cross-sectional view of a base microcatheter of the present disclosure, wherein the base microcatheter includes an internally beveled surface configured to engage a detachable tip, as described herein. Base microcatheter 100 comprises a shaft 102 having a first end 104 and a second, distal, end 106. First end 104 of shaft 102 includes a coupling mechanism 108 (e.g., a beveled hub with integrated Luer lock) configured to engage with one or more different pieces of equipment (e.g., a Luer lock syringe) configured to introduce material (e.g., embolic agents) into and through shaft 102 to exit the second end 106 of microcatheter 100. Base microcatheter 100 may comprise any suitable material for the present application and, in embodiments, includes a material compatible for the delivery of embolic agents containing EVOH in a dimethyl sulfoxide solvent.

Second end 106 of base microcatheter 100 may incorporate radio-opaque elements 110 that may be utilized during a procedure to observe the position and movement of the base microcatheter 100 within a blood vessel, thereby enabling more accurate placement of base microcatheter 100 at the desired procedure site.

The second end 106 of base microcatheter 100 is shaped into a slot 112 to receive a detachable microcatheter tip assembly (e.g., detachable microcatheter tip 200 of FIG. 2, 3, or 4) via a friction-fit or other, suitable, detachable coupling. In an embodiment, the side walls 114 of base microcatheter shaft 100 are sized at second end 106 of shaft 102 so that an interior diameter of side walls 114 ($d_{internal}$) is approximately equal to the external diameter ($d_{external}$, see FIG. 2) of the detachable microcatheter tip, thereby enabling a friction coupling between base microcatheter 100 shaft 102 and the detachable microcatheter tip.

Figure 2:
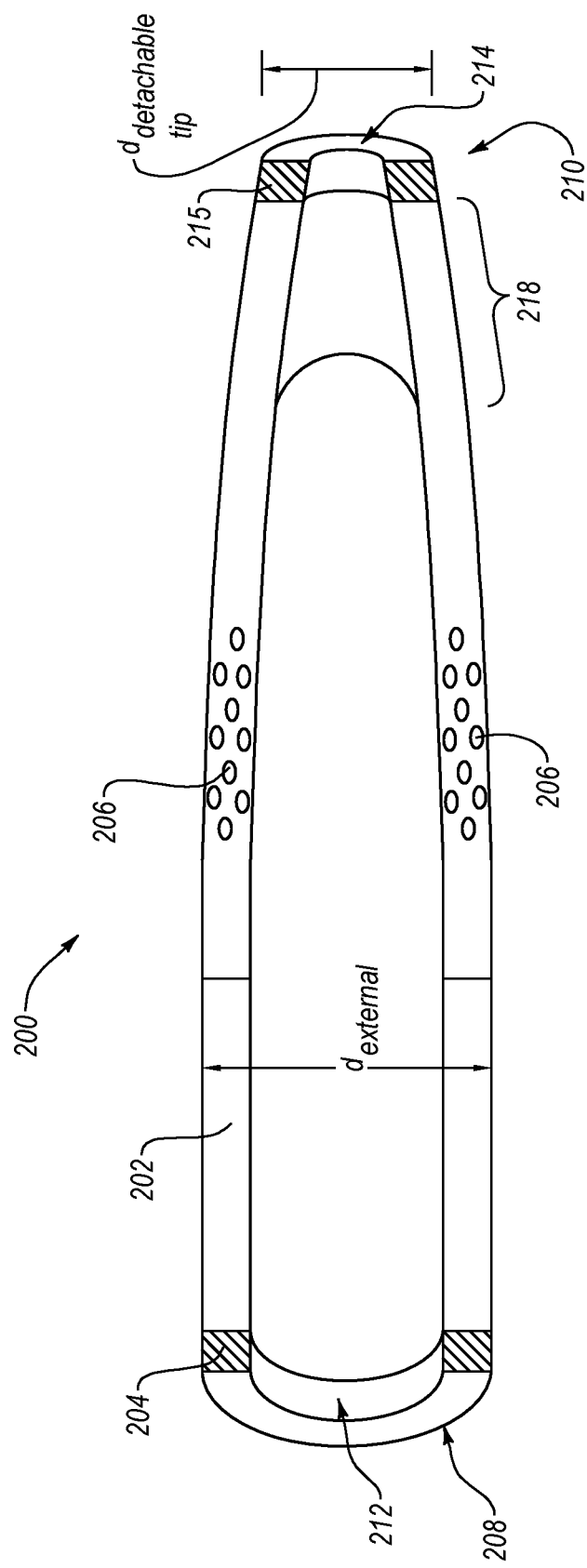
FIG. 2 is a cross-section view of a detachable microcatheter tip that is configured to be detachably retained within an end of the base microcatheter of FIG. 1.

FIG. 2 is a cross-section view of detachable microcatheter tip 200 that is configured to be detachably retained within the second end 106 of base microcatheter 100 shown in FIG. 1. A body 202 of detachable microcatheter tip 200 has an outer diameter that is approximately equal to the inner diameter of second end 106 of base microcatheter 100, enabling detachable microcatheter tip 200 to be engaged with the second end 106 via a friction fit. Detachable microcatheter tip 200 may be constructed from biocompatible material allowing detachable microcatheter tip 200 to be left in-place following a procedure. Example biocompatible materials may include non-degradable polymers like polyethylene block amides (including brand name PEBAX) and biodegradable materials such as DLPLA poly (dl-lactide), LPLA (poly (l-lactide), PGA-polyglycolide, PDO-poly (dioxanone), PGA-TMC-poly(glycolide-co-trimethylene carbonate), PGA-LPLA, PGA-DLPLA, LPLA-DLPLA, PDO-PGA-TMA. The polyhydroxyalkanoate class of biopolymers may also be a suitable biodegradable material for construction of detachable microcatheter tip 200.

Although in the present embodiment, detachable microcatheter tip 200 is configured to engage with base microcatheter 100 via a friction coupling, it should be understood that detachable microcatheter tip 200 may be detachably coupled to base microcatheter by other means. For example, detachable microcatheter tip 200 may couple to base microcatheter 100 via an adhesive or mechanical coupling that is configured to break, fail, or otherwise allow detachment of detachable microcatheter tip 200 under relatively low traction forces (20 to 60 gram-force). In some embodiments, detachable microcatheter tip 200 may be formed integrally with base microcatheter 100 at a frangible connection region (e.g., comprising a thinner wall or weaker material) that, under relatively low traction forces (20 to 60 gram-force), fractures or tears causing detachment of detachable microcatheter tip 200 from base microcatheter 100.

Detachable microcatheter tip 200 may incorporate a band 204 of radio-opaque material at a first end 208 enabling a position of detachable microcatheter tip 200 to be observed and monitored during a procedure. Similarly, detachable microcatheter tip 200 may incorporate a band 216 of radio-opaque material at a second end 210 further enabling a position of detachable microcatheter tip 200 to be observed and monitored during a procedure.

A number of side or lateral-holes 206 are formed about the body 202 of detachable microcatheter tip 200 between first end 208 and second end 210 of detachable microcatheter tip 200. As described herein, lateral side holes 206 are configured to allow passage of embolic agent through lateral holes 206 enabling the formation of an anti-reflux plug of embolic agent during a procedure. Lateral holes 206 may be arranged in any suitable pattern or configuration for the deposition of embolic agent about a perimeter of detachable microcatheter tip 200.

As illustrated in FIG. 2, body 202 of detachable microcatheter tip 200 is generally shaped so that an outer surface of the first end 208 has a shape matching the inner surface of second end 106 of microcatheter 100, enabling detachable microcatheter tip 200 to couple with second end 106 of microcatheter 100 and be retained therein via a friction coupling. In an embodiment, both the outer surface of the first end 208 and the inner surface of second end 106 have uniform diameters. The second end 210 of detachable microcatheter tip 200 may be tapered as illustrated in FIG. 2, or may have any other suitable shape.

Lateral holes 206 are located on body 202 such that when detachable microcatheter tip 200 is coupled to second end 106 of microcatheter 100, lateral holes 206 are located outside of the second end 106 of microcatheter 100 enabling liquid embolic material to flow out of lateral holes 206 even when detachable microcatheter tip 200 is coupled to base microcatheter 100.

Body 202 of detachable microcatheter tip 200 is generally hollow enabling passage of material (e.g., a liquid embolic agent) through a first opening 212 in the first end 208 of detachable microcatheter tip 200, through the body 202, and out of a second opening 214 at the second end 210 of detachable microcatheter tip 200. When the second opening 214 is blocked or otherwise obstructed, the liquid embolic agent may preferentially flow through lateral holes 206.

Body 202 of detachable microcatheter tip 200 defines a loading region 218 internal to body 202 configured to receive a membrane carrier (e.g., membrane carriers 500 of FIGS. 5 and 6 or membrane carrier 700 of FIGS. 7 and 8), described below.

In some embodiments, detachable microcatheter tip 200 may incorporate a parachute structure (also referred to herein as a "flow disrupter mechanism") to further control coherent growth of an anti-reflux plug around the shaft of the detachable tip, and prevent dispersion of liquid embolic agent exiting the detachable tip lateral holes into the adjacent flow stream of circulating blood. The flow disrupter is generally configured so that the flow of embolic agent exiting detachable microcatheter tip 200 via lateral holes 206 is preferentially constrained to a region proximate lateral holes 206. In embodiments, the flow disrupter may be further configured to prevent or inhibit flow of embolic agent towards the distal tip or second end 210 of detachable microcatheter tip 200.

Figure 3:
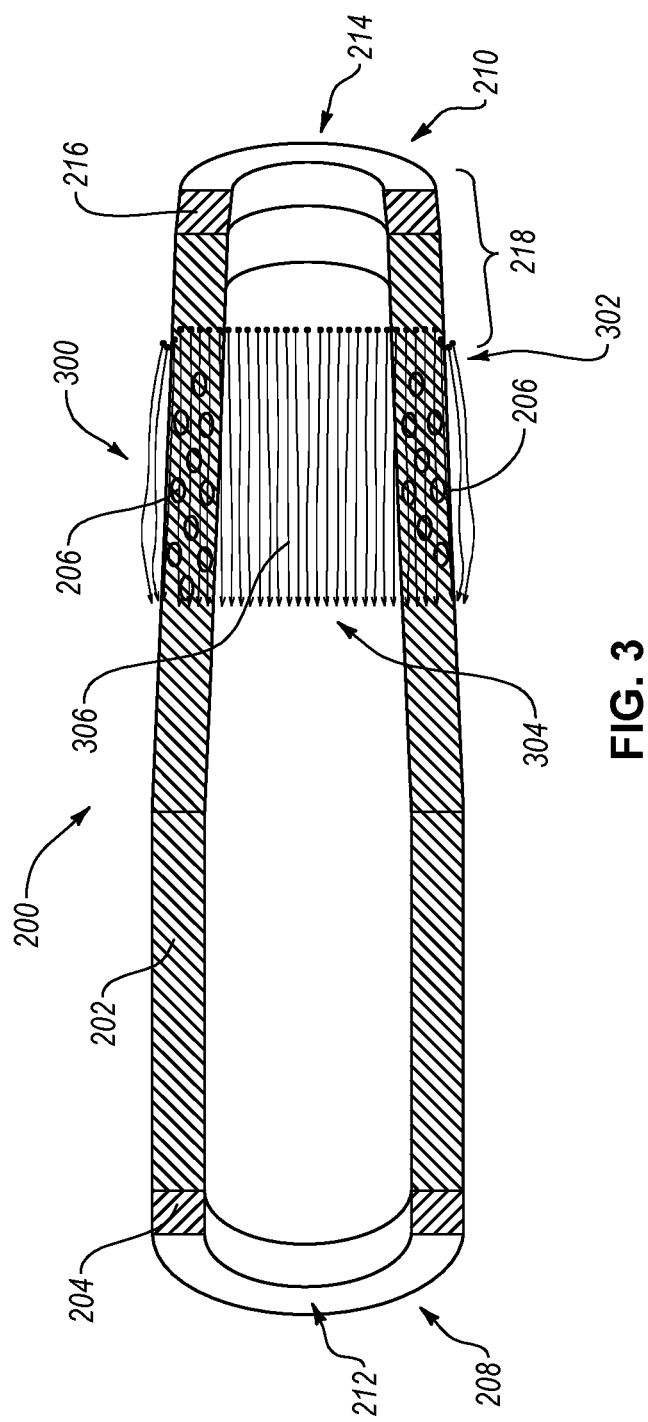
FIGS. 3 and 4 are cross-sectional views of the detachable microcatheter tip of FIG. 2 including a flow disrupter to provide coherent growth of an anti-reflux plug from liquid embolic agent extruded through the detachable tip side holes, where
Figure 4:
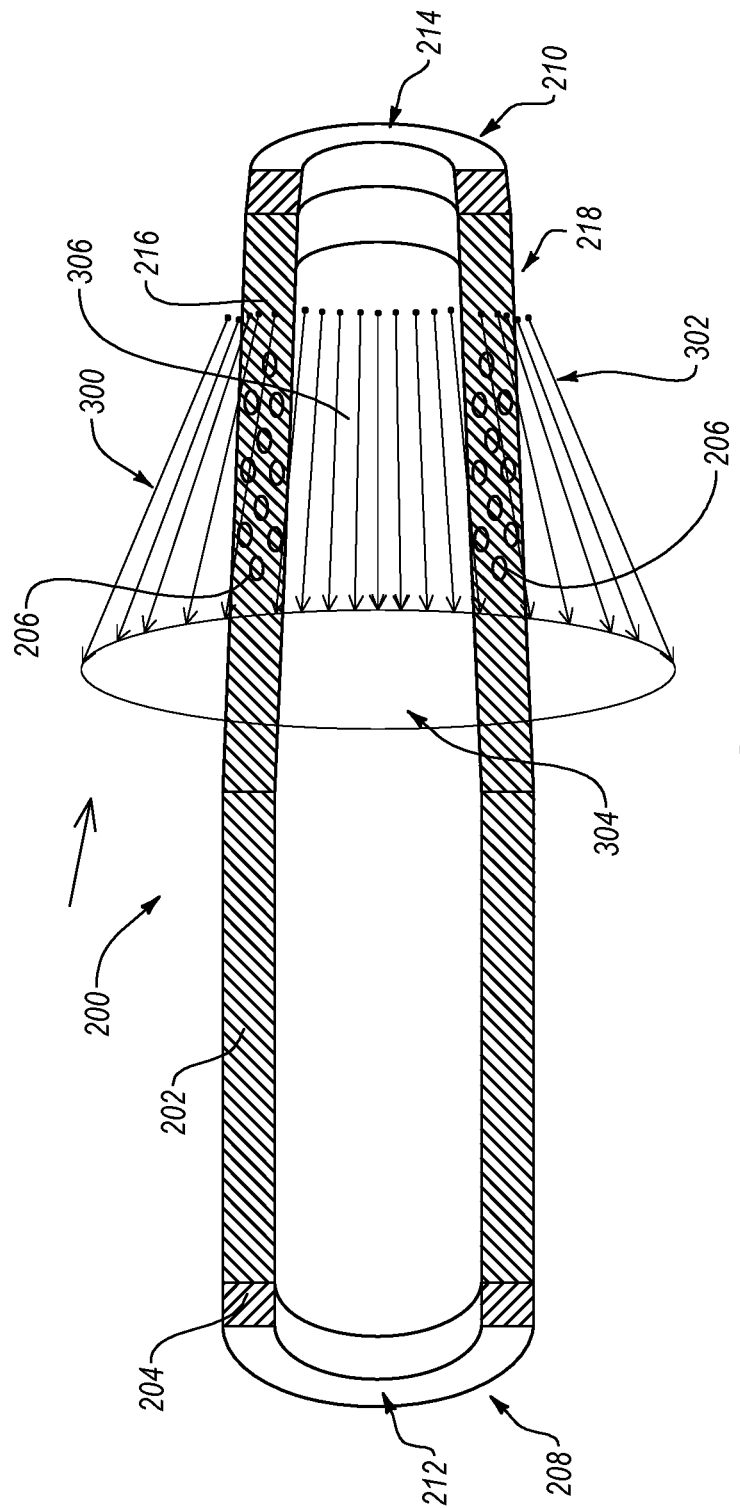

FIGS. 3 and 4 are cross-sectional views of the detachable microcatheter tip 200 including a flow disrupter mechanism configured as a parachute structure to facilitate coherent growth of an anti-reflux plug around the shaft of the detachable tip 200, where FIG. 3 depicts the parachute structure in a closed configuration, while FIG. 4 depicts the parachute structure in an open or deployed configuration.

Parachute structure 300 may be comprised of any suitable materials such as a ribbed elastomeric semi-permeable or microporous or impermeable membrane. In embodiments, structure 300 may comprise a material that is permeable to or configured to absorb or selectively transmit the embolic agent or components thereof. For example, structure 300 may comprise a material permeable to or configured to absorb only the solvent components of the embolic agent to facilitate curing and/or hardening of the embolic agent proximate to structure 300. A first end 302 of parachute structure 300 encircling body 202 is attached to body 202 of detachable microcatheter tip 200, while a second end 304 of parachute structure encircling body 202 is unattached to body 202. The first end 302 of parachute structure 300 is attached to body 202 in a manner enabling the second end 304 of the parachute structure 300 to move relative to body 202, thereby enabling the parachute structure to move from a closed position (depicted in FIG. 3) to an open position (depicted in FIG. 4). In its closed position, as illustrated in FIG. 3, parachute structure 300 overlays or covers lateral holes 206 of detachable microcatheter tip 200.

To provide structure and/or support to parachute structure 300, parachute structure 300 may incorporate a number of shape memory ribs 306 running a length of parachute structure. Ribs 306 may comprise a shape memory materials, including, for example, various metal alloys such as a Nickel Titanium alloy (NiTiNOL). Ribs 306 may be configured so that during positioning of detachable microcatheter tip 200 within the body, ribs 306 are crimped or biased to retain parachute structure 300 in the closed position as depicted in FIG. 3. However, once embolic agent flows out of lateral holes 206 and pushes parachute structure 300 in its closed position away from the body of detachable microcatheter tip 200, ribs 306 may be configured to change configuration to bias parachute structure 300 into the open configuration, as depicted in FIG. 4. In this manner, while embolic agent is flowed through lateral holes 206, the second end 305 of parachute structure 300 is biased against the internal circumference of the vessel thereby inhibiting or preventing the flow of embolic agent towards the distal tip or second end 210 of detachable microcatheter tip 200.

During use of a detachable microcatheter tip 200 that incorporates parachute structure 300, initially, parachute structure 300 is in its closed configured (e.g., during first positioning or placement of detachable microcatheter tip 200), as illustrated in FIG. 3. During deposition of embolic fluid through lateral holes 206, however, the embolic fluid interacts with parachute structure 300 and pushes parachute structure 300 into its open position (e.g., as illustrated in FIG. 4), which action may be assisted by memory shape materials, such as ribs 206. With parachute structure 300 so deployed, dispersion of liquid embolic agent into the anterograde flow stream of circulating blood is prevented to improve the formation of a coherent anti-reflux plug.

During such a procedure, to promote initial flow of embolic material through side holes of detachable microcatheter tip 200 rather than the second opening 214 at the second end 210 of detachable microcatheter tip 200, material flow through the second opening 214 may be inhibited by a membrane that covers the second opening 214. The membrane may be configured to rupture or become displaced once sufficient material has passed through lateral holes 206 enabling an anti-reflux plug to be formed and solidify, thereby obstructing further movement of liquid embolic agent through the lateral holes of the detachable tip. Once ruptured, materials can pass through the ruptured membrane and out of second opening 214 of detachable microcatheter tip 200.

In an embodiment, the membrane may be incorporated into a membrane carrier structure that can be selectively positioned within body 202 of detachable microcatheter tip 200 so as to cover or inhibit flow of material through second opening 214.

Figure 5:
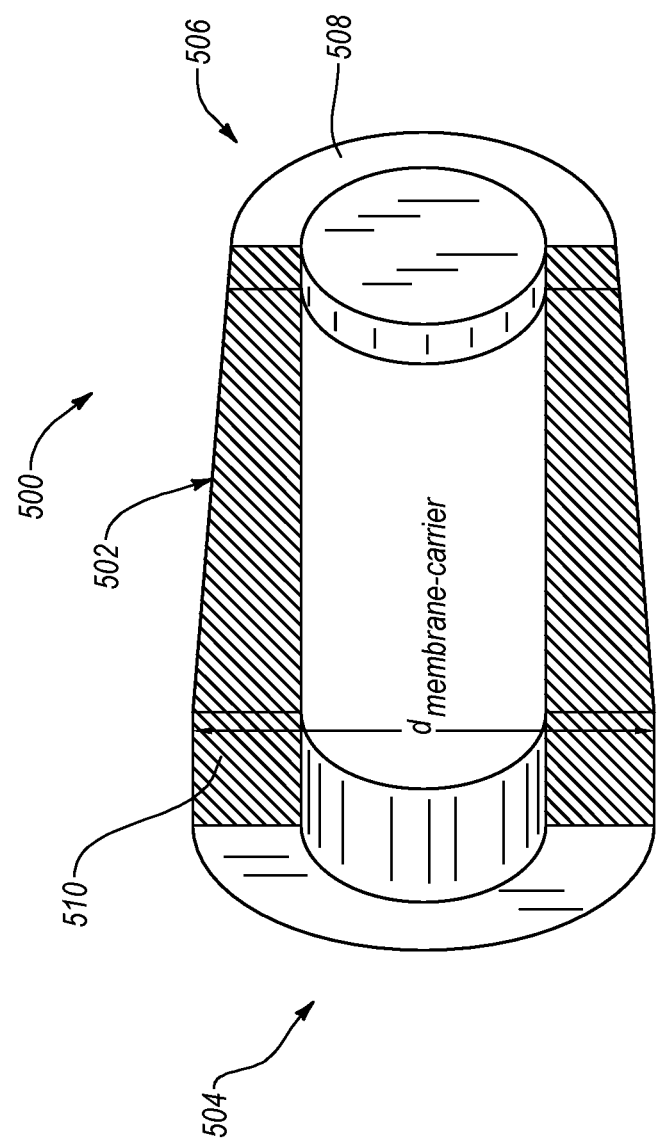
FIG. 5 is a cross-sectional view of a membrane carrier, where the membrane carrier is configured to be positioned within a loading region of the detachable microcatheter tip of FIGS. 2-4 to seal or cover an opening of the detachable microcatheter tip.
Figure 6:
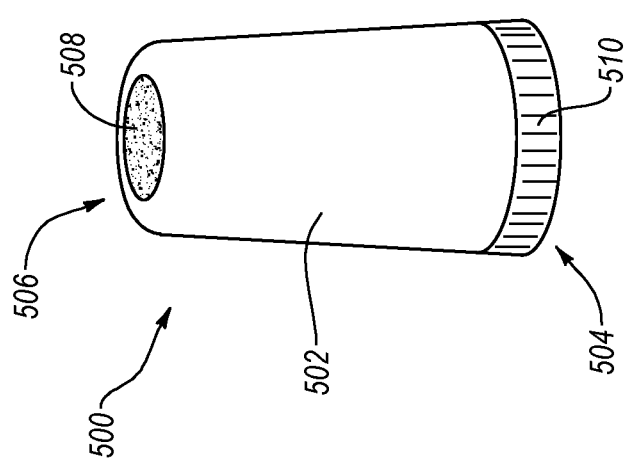
FIG. 6 is a perspective view of the membrane carrier of FIG. 5.

FIG. 5 is a cross-sectional view of membrane carrier 500, where membrane carrier 500 is configured to be positioned within loading region 218 of detachable microcatheter tip 200 to seal or cover second opening 214. FIG. 6 is a perspective view of membrane carrier 500 of FIG. 5.

Membrane carrier 500 includes a body 502 defining a central cavity. Body 502 is tapered so that a first end 504 of body 502 has a wider diameter than a second end 506 of body 502. Body 502 defines a central cavity and openings at each of first end 504 and second end 506. Body 502 may include a metallic or polymeric material.

The opening at second end 506 of body 502 of membrane carrier 500 is covered and/or sealed by a pressure sensitive and impermeable membrane 508. Membrane 508 is configured to break or open during use of the present microcatheter system when an embolic agent presses against membrane 508 with sufficient force, thereby allowing embolic agent to flow through the opening of second end 506 of membrane carrier 500 when membrane 508 is broken. During some operations, membrane 508 may be configured to break at pressures of around 100-500 pounds per square inch (PSI), though different membranes 508 with different breaking pressures may also be utilized.

First end 504 of membrane carrier 500 may incorporate radio-opaque elements 510 that may be utilized during a procedure to observe the position and movement of membrane carrier 500, thereby enabling more accurate and easy placement of membrane carrier 500 in the loading region 218 of detachable microcatheter tip 200.

The shape of body 502 of membrane carrier 500 is selected to retain membrane carrier 500 within the loading region of detachable catheter tip 200. Specifically, in the depicted embodiment the conical shape of membrane carrier 500 allows the second end of membrane carrier 500 carrier membrane 508 to protrude out of the second opening 214 at the second end 210 of detachable microcatheter tip 200. At the same time, the wider first end 506 of membrane carrier ($d_{membrane\_carrier}$, FIG. 5) is too wide to pass through second opening 214 ($d_{detachable\_tip}$, FIG. 2), effectively retaining membrane carrier 500 within the loading region of detachable catheter tip 200.

Figure 7:
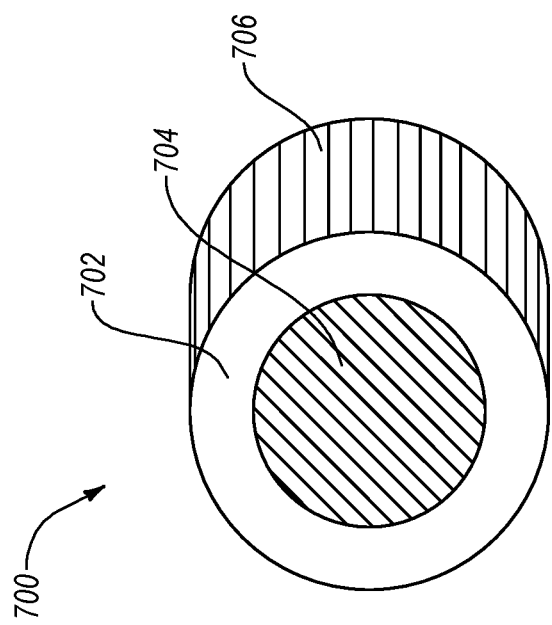
FIG. 7 is a perspective view of a membrane carrier, where the membrane carrier has a disc shape and is configured to be positioned within loading region of a detachable microcatheter tip to seal or cover an opening of the detachable microcatheter tip.

In other embodiments, a membrane carrier may instead be formed in a disc shape that enables placement within a detachable catheter tip. For example, FIG. 7 is a perspective view of membrane carrier 700, where membrane carrier 700 is configured to be positioned within loading region 218 of detachable microcatheter tip 200 to seal or cover second opening 214.

Membrane carrier 700 includes a body 702 defining a central cavity. Body 702 is shaped as a disc with a central opening. Body 702 may include a metallic or polymeric material.

The opening in body 702 is covered and/or sealed by a pressure sensitive and impermeable membrane 704. Membrane 704 is configured to break or open during use of the present microcatheter system when an embolic agent presses against membrane 704 with sufficient force, thereby allowing embolic agent to flow through body 702. During some operations, membrane 704 may be configured to break at pressures of around 100-500 pounds per square inch (PSI), though different membranes 704 with different breaking pressures may also be utilized.

Body 702 of membrane carrier 700 may incorporate radio-opaque materials 706 that may be utilized during a procedure to observe the position and movement of membrane carrier 700, thereby enabling more accurate and easy placement of membrane carrier 700 in the loading region 218 of detachable microcatheter tip 200.

Figure 8:
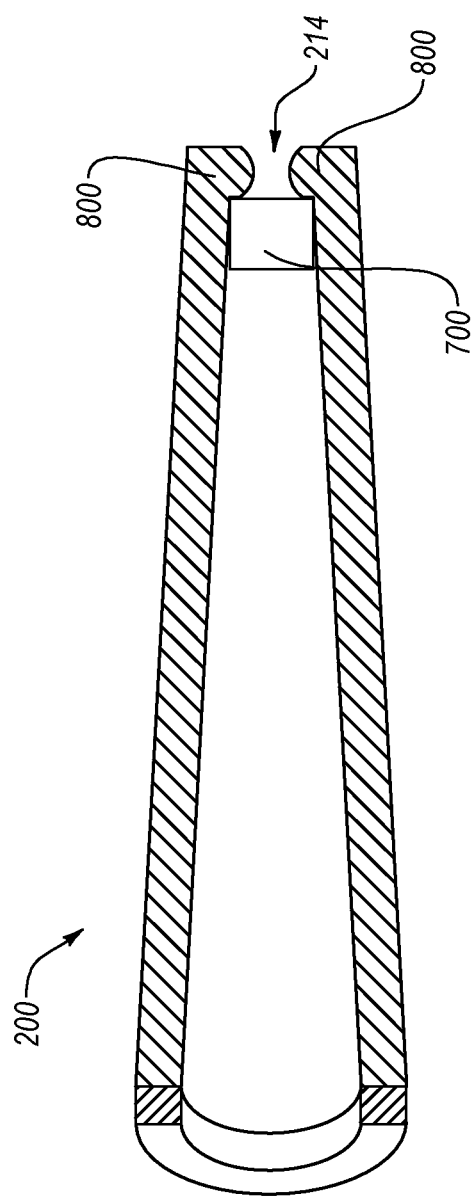
FIG. 8 is a simplified illustration of the detachable microcatheter tip of FIG. 2 modified to include a retention mechanism for retaining the membrane carrier of FIG. 7.

To retain membrane carrier 700 within the loading region 218 of detachable microcatheter tip 200, the opening 214 at the second end 210 of detachable microcatheter tip 200 may be modified to incorporate a retention structure. To illustrate, FIG. 8 is a simplified illustration of detachable microcatheter tip 200 of FIG. 2 modified to include a retention mechanism for retaining membrane carrier 700. As shown in FIG. 8, retention structure 800 is formed around an interior surface of opening 214 of detachable microcatheter tip 200. Retention structure 800 is sized so that membrane carrier 700 cannot pass through opening 214 and instead, membrane carrier 700 pushes up against retention structure 800, effectively sealing the opening 214 of detachable microcatheter tip 200 until the membrane 704 of membrane carrier 700 ruptures.

Figure 9:
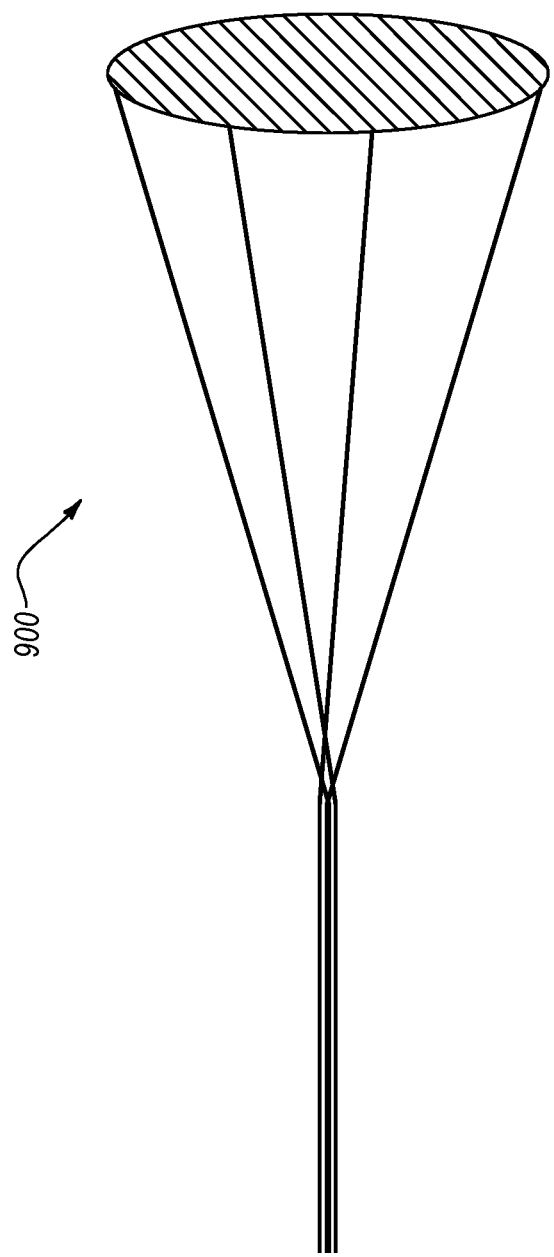
FIG. 9 depicts an example pusher wire tool that may be used to deploy one of the membrane carriers of FIGS. 5-7 through the base microcatheter into a detachable microcatheter tip.

Any suitable method may be used to deposit either of membrane carriers 500 or 700 in detachable microcatheter tip 200. For example, fluid flushing could be used to advance a membrane carrier through a microcatheter and into a loading region of a detachable microcatheter tip coupled to the microcatheter as described herein. Alternatively, or in combination with fluid flushing, a mechanism or device may be used to facilitate positioning of the membrane carriers. For example, FIG. 9 depicts an example pusher wire tool 900 that may be used to deploy one of the membrane carriers of FIGS. 5-7 through base microcatheter into a coupled detachable microcatheter tip. Tool 900 includes a pusher wire and a conical element sized to mate with either of membrane carrier 500 or 700 enabling the membrane carrier 500 or 700 to be introduced and advanced through the base microcatheter and into the detachable microcatheter tip.

In various other embodiments, membrane carrier 500 or 700 may be formed integrally in the loading region 218 of detachable microcatheter tip 200.

Figure 10:
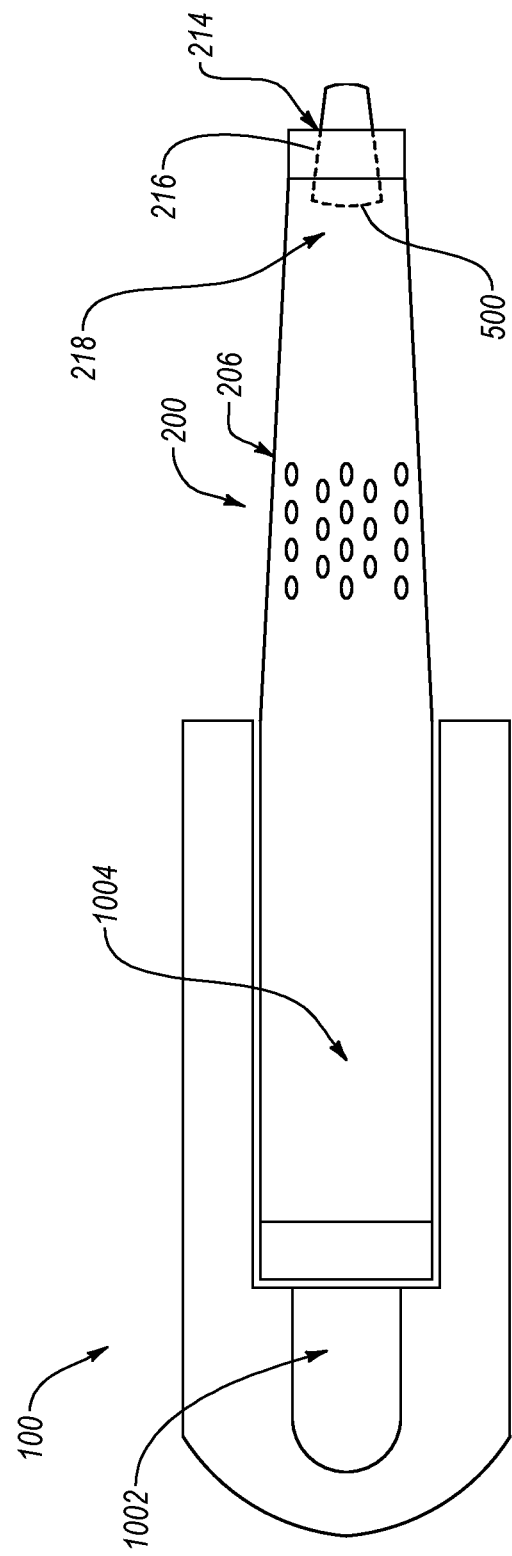
FIG. 10 is a cross-sectional view depicting an assembled system in which a detachable microcatheter tip is coupled to an end of a base microcatheter.
Figure 11A:
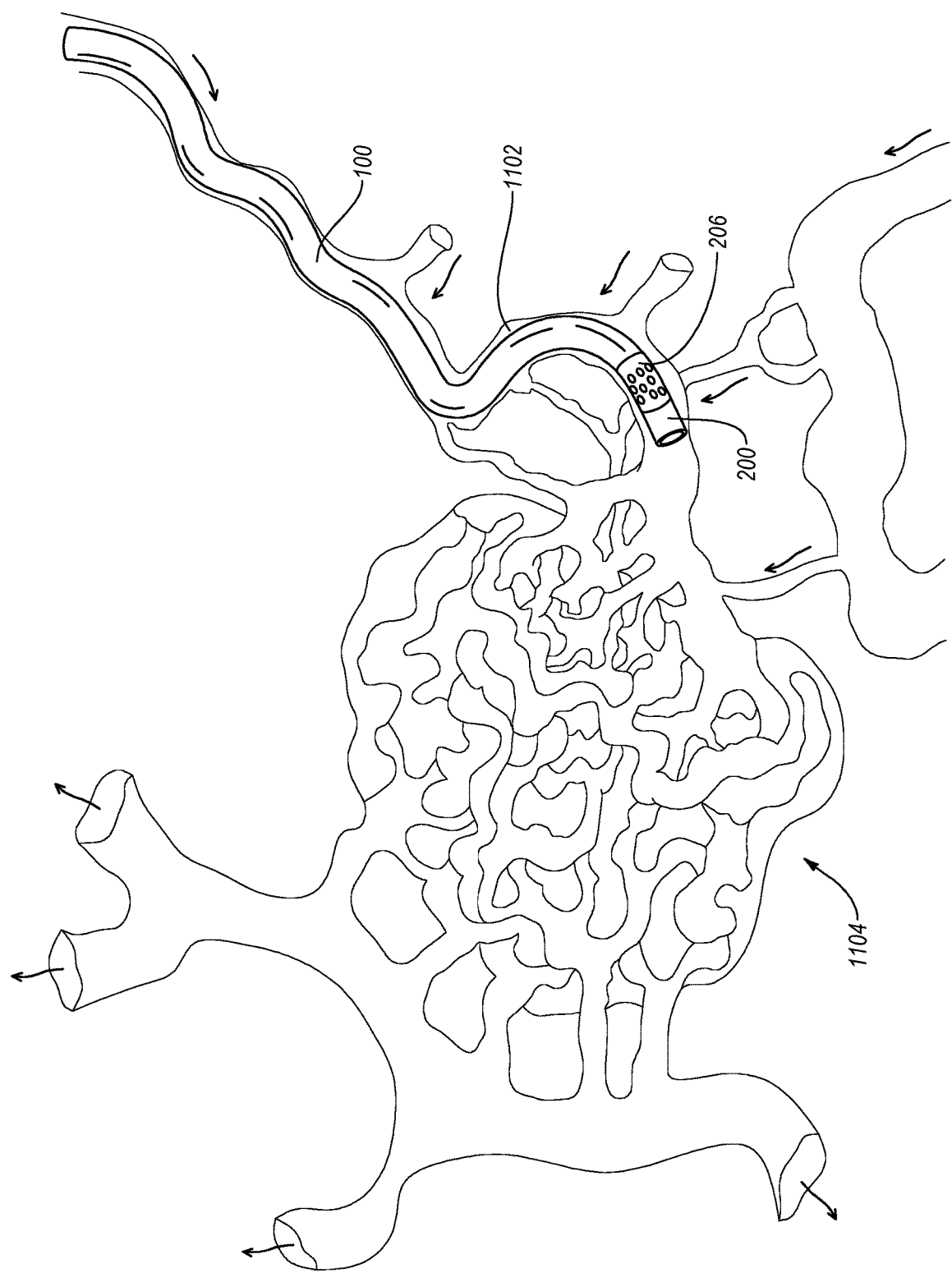
FIGS. 11A-11F are a sequence of images depicting a procedure.
Figure 11B:
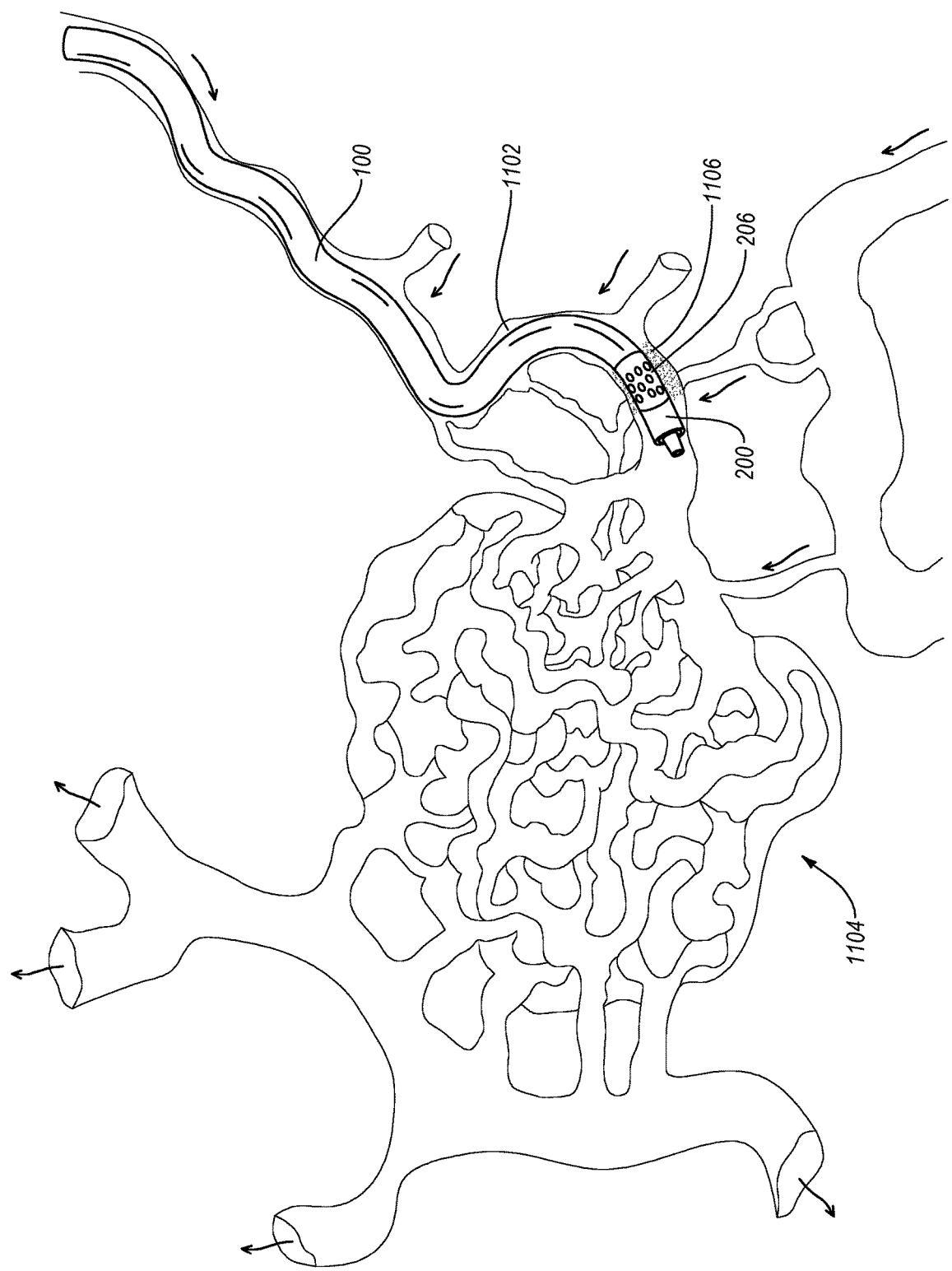
Figure 11C:
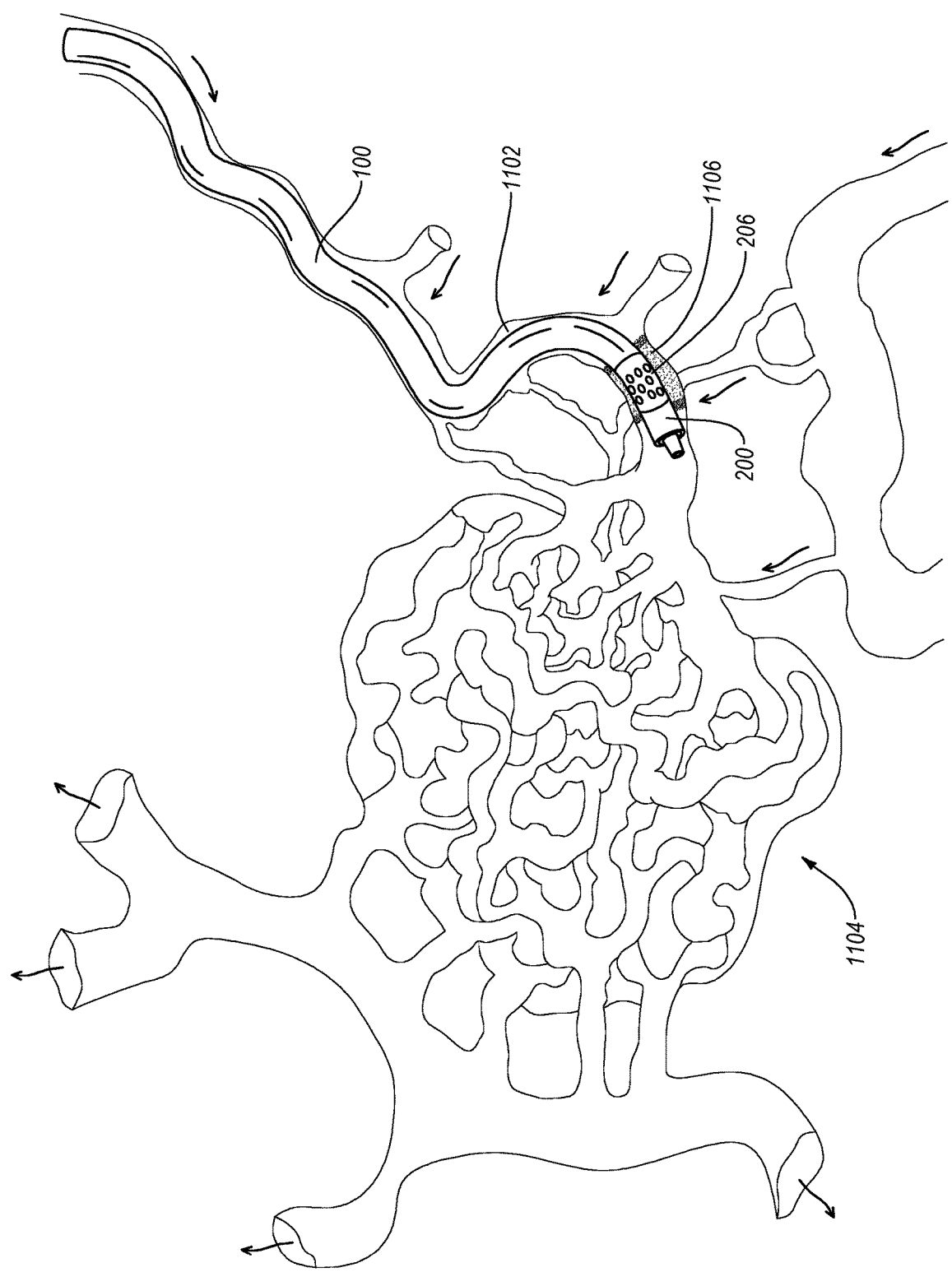
Figure 11D:
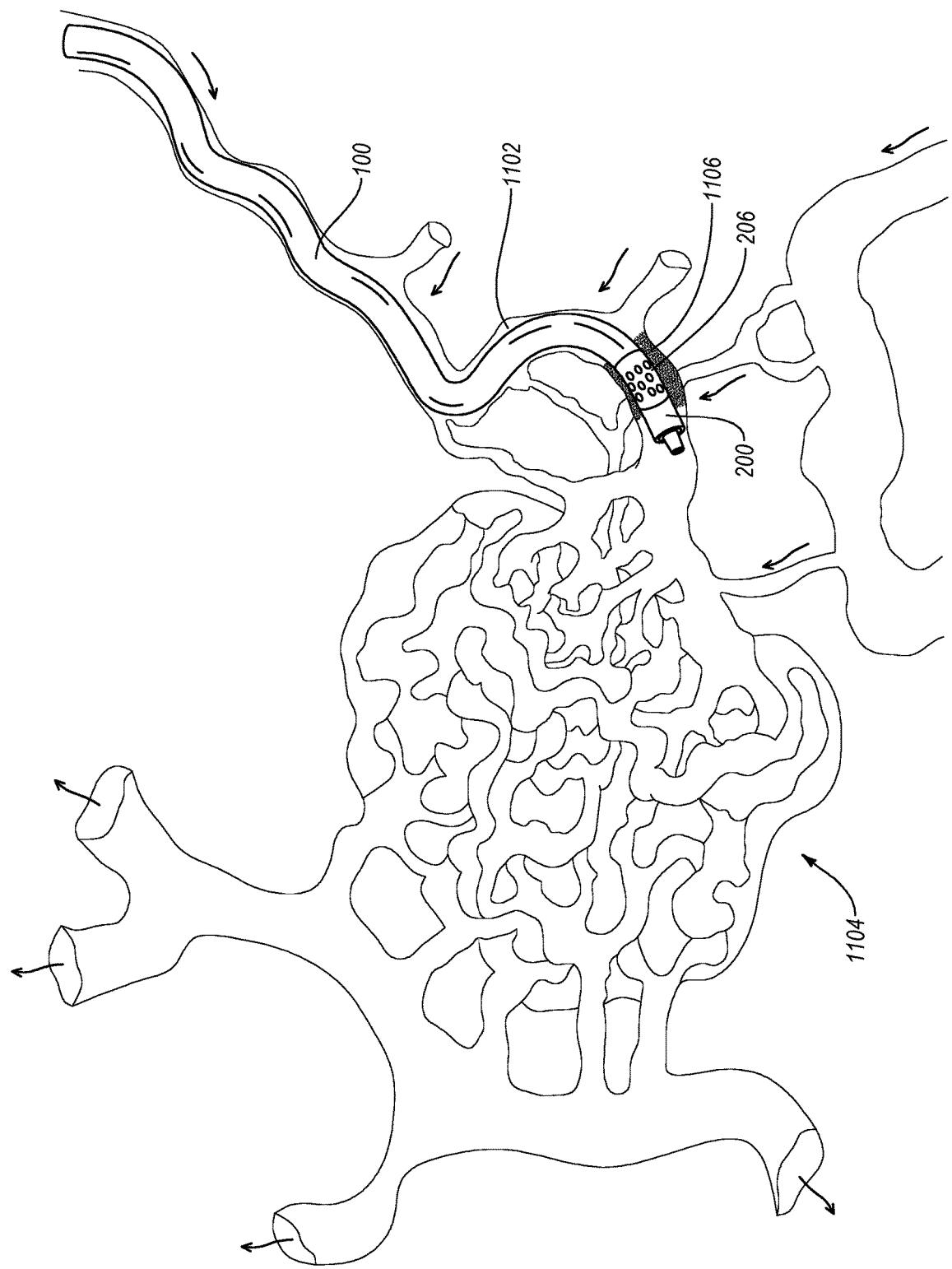
Figure 11E:
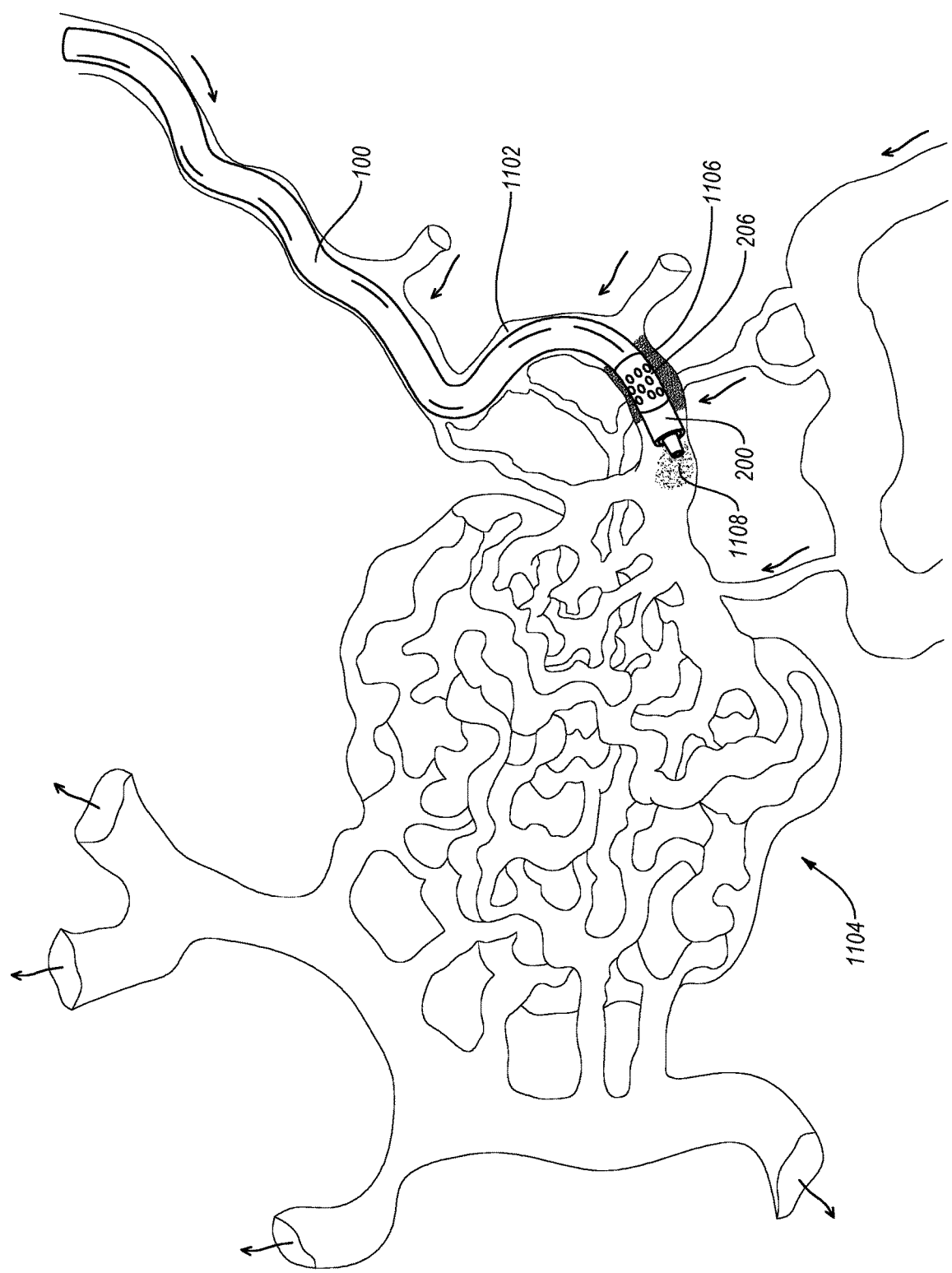
Figure 11F:
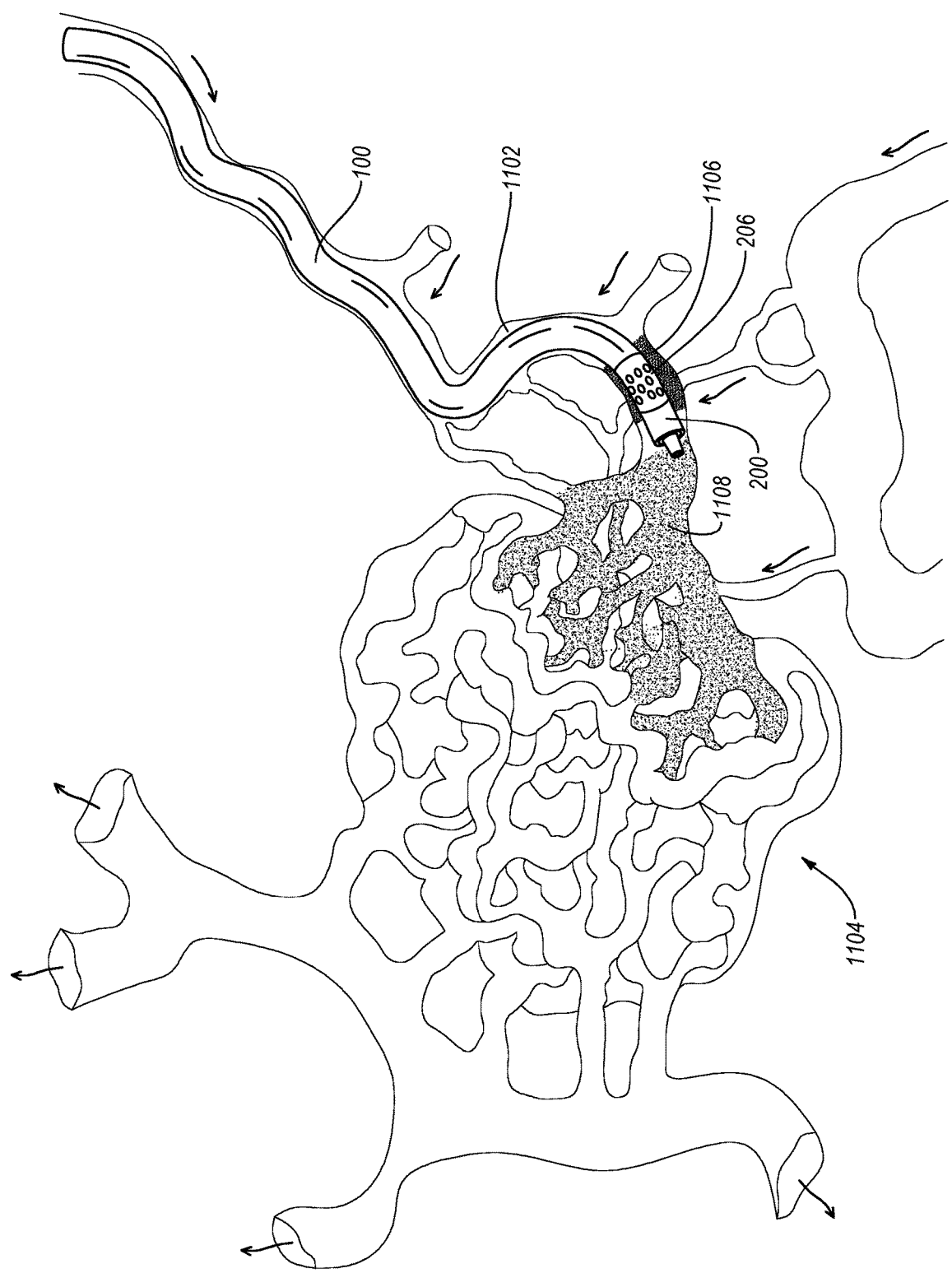

FIG. 10 is a cross-sectional view depicting an assembled system in which detachable microcatheter tip 200 is coupled to an end of base microcatheter 100 and membrane carrier 500 is positioned within an end hole of detachable microcatheter tip 200. In this configuration, detachable microcatheter tip 200 is coupled to base microcatheter 100 in a manner enabling detachable microcatheter tip 200 to separate from base microcatheter 100 at the conclusion of a procedure and, specifically, in cases where detachable microcatheter tip 200 is adhering to solidified embolic materials that have been dispensed through detachable microcatheter tip 200. Additionally, lateral holes 206 are exposed when detachable microcatheter tip 200 is coupled to base microcatheter 100 in this manner allowing embolic agent to flow through lateral holes 206 during an initial stage of the procedure.

In this arrangement, a central lumen 1002 of base microcatheter 100 is in fluid communication with the central lumen 1004 of detachable microcatheter tip 200. As such, a membrane carrier (e.g., membrane carrier 500 or 700) can be introduced through lumen 1002 of base microcatheter 100 and lumen 1004 of detachable microcatheter tip 200 and into loading region 218 enabling a membrane carrier, so disposed, to block opening 214 until the membrane of the membrane carrier ruptures.

Operation

Figure 13:
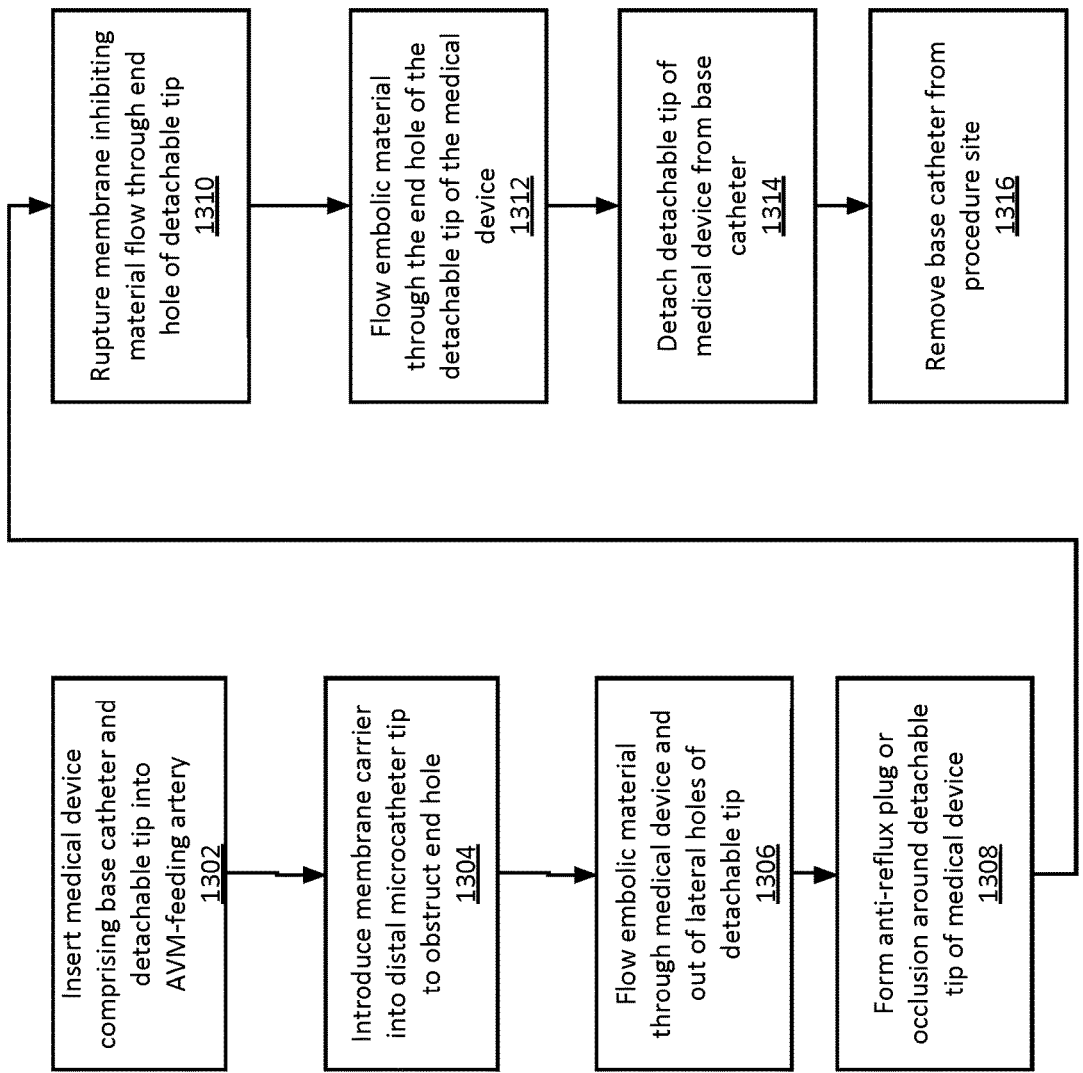
FIG. 13 is a flowchart depicting steps of an example procedure implemented using the present system.

FIGS. 11A-11F are a sequence of images depicting a procedure implemented using the present system. FIG. 13 is a flowchart depicted depicting steps of the example procedure implemented using the present system. During the example procedure, in an initial step 1302 the internally beveled base microcatheter 100 is navigated over a microguidewire into an AVM feeding artery 1102 using fluoroscopic guidance. A tapered detachable microcatheter tip 200 with or without parachute flow disruptor modification (e.g., as shown in FIGS. 4 and 5) is pre-installed into the slotted cove of base microcatheter 100 such that a solitary unit (e.g., as depicted in FIG. 10) comprises the combination of base microcatheter 100 and detachable microcatheter tip 200. In step 1304, a membrane carrier 500 or 700 (not shown in FIGS. 11A-11F) is introduced into the proximal beveled hub microcatheter 100 and advanced through the shaft or lumen of base microcatheter 100, into the luminal channel of detachable microcatheter tip 200 to the distal loading region 218 of detachable microcatheter tip 200. The membrane carrier 500 or 700 can be advanced using fluid flushes and/or conical pusher wire tool 900. The microcatheter assembly thus reconstituted in situ is then ready to perform fluoro-surgically guided embolization.

The luminal topographic architecture of the base microcatheter 100 is designed to 1) create a slot to mate with the detachable microcatheter tip 200 and form a friction lock, 2) establish a flush lumen that is continuous between and across the junction zone from base microcatheter 100 to detachable microcatheter tip 200 so that the membrane carrier vehicle 500 or 700 slides across into the loading region 218. The topographical architecture of the membrane carrier vehicle 500 or 700 is designed to mate into the lumen of the base microcatheter.

The topographical architecture of the detachable microcatheter tip 200 is designed to be flush with that of the base microcatheter 100 on the proximal side, and taper on the distal side of the loading region 218 for the membrane carrier 500 or 700 so that the membrane carrier 500 or 700 is constrained in the loading region 218 of the detachable microcatheter tip 200.

During operation of the present microcatheter system, the detachable microcatheter tip 200 is coupled to the base microcatheter 100 and a membrane carrier 500 or 700 is disposed in a proximal end of the detachable microcatheter tip 200 to prevent the flow of material through the end hole of the detachable microcatheter tip 200. With the assembled system positioned proximate to an AVM 1104 (FIG. 11A), in step 1306 embolic material is flowed or injected through the lumen of the base microcatheter 100 into the interior lumen of the detachable microcatheter tip 200. Because the end hole is blocked, in step 1308 initially embolic material flows out through the lateral holes 206 of detachable microcatheter tip 200 to initially form a tightly focused, coherent copolymer anti-reflux plug 1106 (FIGS. 11B-11F) around the proximal shaft of the detachable microcatheter tip 200. With the anti-reflux plug formed and fully solidified, addition embolic material is unable to flow out of the lateral holes 206 (which are now blocked), resulting in an increase in pressure internal to the detachable microcatheter tip 200. In step 1310, the pressure increases eventually causing the membrane of the membrane carrier disposed within the detachable microcatheter tip 200 to rupture (FIG. 11E) allowing further embolic material 1108 to flow through the distal opening of the detachable microcatheter tip 200 (FIG. 11F) in step 1312. Such membrane rupture can open a path for embolic copolymer movement from the end hole opening of the detachable microcatheter tip 200 into the unobstructed vessel lumen distal to the previously solidified anti-reflux plug, which fills the entire cross-section of upstream vessel lumen. Accordingly, further liquid copolymer embolic material can be injected through the distal end-hole of the detachable microcatheter tip 200 and freely moves anterograde into the unobstructed vessel lumen with highly reliable anti-reflux protection. Since no injection pauses are necessary to accommodate reflux, the entire malformation vasculature can be filled with freely flowing liquid embolic agent.

Upon completion of the procedure, the base microcatheter 100 can be detached (step 1314) and removed from the procedure site (step 1316). Upon removal, the detachable microcatheter tip 200 may separate from the base microcatheter 100, leaving the detachable microcatheter tip 200 in place.

In some embodiments, the membrane of the present system may be implemented in the form of a bubble delivered into the device's detachable microcatheter tip. The bubble may be configured to block or obscure the end opening of the microcatheter tip when embolic agent is first injected or flowed through the detachable microcatheter tip through the tip's side opening. When an appropriate anti-reflux plug is formed by the embolic agent, additional pressure may be applied to the membrane causing the bubble to either burst or be forced out of the end opening in the detachable microcatheter tip. This then enables a conventional delivery of embolic agent through the end opening of the detachable microcatheter tip as described herein.

Figure 12:
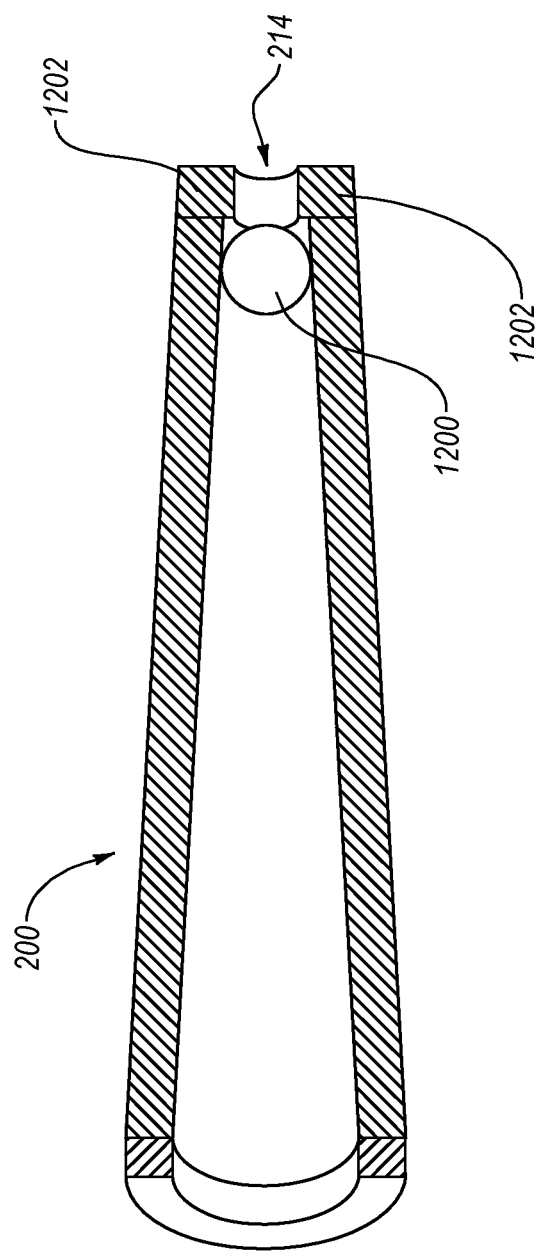
FIG. 12 depicts a cross-sectional view of a detachable microcatheter tip incorporating a retention structure enabling a bubble to form a temporary seal over an end opening of the detachable microcatheter tip.

To illustrate this embodiment, FIG. 12 depicts a cross-sectional view of detachable microcatheter tip 200 incorporating a retention structure enabling a bubble 1200 formed as described herein to form a temporary seal over an end hole opening of the detachable microcatheter tip.

In this embodiment, bubble 1200 may be formed and deposited within detachable microcatheter tip 200 using any suitable method or approach. In one case, bubble 1200 may be a micro-bubble formed by ultrasound activation. The bubble 1200 may be formed directly within detachable microcatheter tip 200. Alternatively, bubble 1200 may be formed elsewhere, such as within the lumen running through the base microcatheter 100 shaft 102, or even external to base microcatheter 100, and then guided through shaft 102 of base microcatheter 100 into the internal volume of detachable microcatheter tip 200.

Bubble 1200 may be filled with air or bubble 1200 may be formed using other gases. In embodiments, bubble 1200 may include gases that are safe to be absorbed by nearby tissue. Example gases may include oxygen, carbon dioxide, perfluorocarbons or fluorocarbons or noble gases, such as Xenon. By controlling the gases contained within bubble 1200 attributes such as the absorbability of bubble 1200 and the strength or fracturing pressure of bubble 1200 can be further controlled.

To retain bubble 1200 within the loading region 218 of detachable microcatheter tip 200, the opening 214 at the second end 210 of detachable microcatheter tip 200 may be modified to incorporate a bubble retention structure. To illustrate, FIG. 12 is a simplified illustration of detachable microcatheter tip 200 of FIG. 2 modified to include a retention mechanism for retaining bubble 1200. As shown in FIG. 12, retention structure 1202 is formed around an interior surface of opening 214 of detachable microcatheter tip 200. Retention structure 1202 is generally shaped as a wall or internally raised surface that is sized so that bubble 1200 cannot pass through opening 214 and instead, bubble 1200 pushes up against retention structure 1202, effectively sealing the opening 214 of detachable microcatheter tip 200 until the bubble 1200 ruptures or is forced, with sufficient pressure, through opening 214 past retention structure 1202. In some embodiments, bubble 1200 may be ruptured, burst or dislodged using the application of an external force (e.g., via ultrasound).

In embodiments, retention structure 1200 may include surface treatments or coatings that can further control the amount of force required to force bubble 1200 through opening 214.

Any suitable method may be used to deposit bubble 1200 in detachable microcatheter tip 200 of FIG. 12. For example, fluid flushing could be used to advance bubble 1200 a microcatheter system and into a loading region of a detachable microcatheter tip coupled to the base microcatheter as described herein. Alternatively, or in combination with fluid flushing, a mechanical device may be used to facilitate positioning of the membrane carriers. In various other embodiments, bubble 1200 may be formed within detachable microcatheter tip 200 when detachable microcatheter tip 200 is outside of a patient's body prior to insertion.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A medical device, comprising:
    a base microcatheter;
    a microcatheter tip assembly detachably coupled to a first end of the base microcatheter, the microcatheter tip assembly including:
        a body defining at least one lateral hole and a loading region, and
        an opening in a first end of the microcatheter tip assembly; and
    a membrane carrier disposed within the loading region of the microcatheter tip assembly, the membrane carrier including:
        a body defining an opening, and
        a membrane covering the opening of the membrane carrier, the membrane being configured to prevent a flow of embolic fluid through the opening in the first end of the microcatheter tip assembly to cause the embolic fluid to flow through the at least one lateral hole of the microcatheter tip assembly until the embolic fluid forms an anti-reflux plug of embolic fluid about the at least one lateral hole that prevents the embolic fluid from further flowing through the at least one lateral hole so that flow of the embolic fluid into the membrane carrier causes a pressure of the embolic fluid within the microcatheter tip assembly to rupture the membrane to allow the embolic fluid to flow through the opening in the first end of the microcatheter tip assembly.

2. The medical device of claim 1, further comprising a flow disrupter coupled to an exterior surface of the microcatheter tip assembly, wherein the flow disrupter is configured to inhibit flow of the embolic fluid from the at least one lateral hole towards the first end of the microcatheter tip assembly and promote coherent growth of the anti-reflux plug from the embolic fluid solidifying.

3. The medical device of claim 2, wherein the flow disrupter includes a parachute structure comprising a first end and a second end, and wherein the first end of the parachute structure is coupled to the body of the microcatheter tip assembly between the at least one lateral hole and the first end of the microcatheter tip assembly.

4. The medical device of claim 3, wherein the parachute structure includes a plurality of ribs, wherein each rib of the plurality of ribs extends from the first end of the parachute structure to the second end of the parachute structure.

5. The medical device of claim 3, wherein the embolic fluid includes a solvent and the parachute structure is configured to absorb the solvent.

6. The medical device of claim 1, wherein the microcatheter tip assembly is removably coupled to the base microcatheter by a friction coupling.

7. The medical device of claim 1, wherein the membrane is configured to rupture when the pressure exceeds 100 pounds per square inch (PSI).

8. The medical device of claim 1, wherein the membrane carrier is formed integrally with the microcatheter tip assembly.

9. The medical device of claim 1, wherein the membrane carrier includes a radio-opaque material.

10. A medical device, comprising:
    a microcatheter tip assembly configured to couple to an end of a microcatheter, the microcatheter tip assembly including:
        a body defining at least one lateral hole and a loading region, and
        an opening in a first end of the microcatheter tip assembly; and
    a membrane carrier configured to be disposed within the loading region of the microcatheter tip assembly, the membrane carrier including:
        a body defining an opening, and
        a membrane covering the opening of in the membrane carrier, the membrane being configured to prevent a flow of embolic fluid through the opening in the first end of the microcatheter tip assembly to cause the embolic fluid to flow through the at least one lateral hole of the microcatheter tip assembly until the membrane ruptures in response to a force applied to the membrane.

11. The medical device of claim 10, further comprising a flow disrupter coupled to the body of the microcatheter tip assembly, wherein the flow disrupter is configured to inhibit flow of the embolic fluid from the at least one lateral hole towards the first end of the microcatheter tip assembly.

12. The medical device of claim 11, wherein the flow disrupter includes a parachute structure comprising a first end and a second end, and wherein the first end of the parachute structure is coupled to the body of the microcatheter tip assembly.

13. The medical device of claim 12, wherein the parachute structure includes a plurality of ribs, wherein each rib of the plurality of ribs extends from the first end of the parachute structure to the second end of the parachute structure.

14. The medical device of claim 10, wherein the microcatheter tip assembly is configured to be removably coupled to the microcatheter by friction.

15. The medical device of claim 10, wherein the membrane is configured to rupture when the force applied to the membrane exceeds 100 pounds per square inch (PSI).

16. The medical device of claim 10, wherein the membrane carrier is formed integrally with the microcatheter tip assembly.

17. A method, comprising:
    inserting a medical device into a vessel, the medical device including a base microcatheter and a detachable tip assembly that is removably coupled to the base microcatheter, the detachable tip assembly comprising a plurality of lateral holes and an end hole covered by a membrane;
    flowing an embolic material through the base microcatheter, the detachable tip assembly, and the plurality of lateral holes to form an anti-reflux plug in the vessel around at least a portion of the detachable tip assembly;

after flowing the embolic material through the plurality of lateral holes, flowing the embolic material further into the detachable tip assembly to cause the membrane to rupture;

after rupturing the membrane, flowing the embolic material through the end hole of the detachable tip assembly anterograde to the anti-reflux plug;

detaching the detachable tip assembly from the base microcatheter; and removing the base microcatheter from the vessel.

18. The method of claim 17, wherein a membrane carrier includes the membrane and the method further comprises disposing the membrane carrier into the detachable tip assembly before flowing the embolic material through the plurality of lateral holes.

* * * * *